(12) United States Patent
Leedham

(10) Patent No.: US 7,585,992 B2
(45) Date of Patent: Sep. 8, 2009

(54) SYNTHESIS OF GALLIUM AND INDIUM ALKOXIDES

(75) Inventor: Timothy Leedham, Suffolk (GB)

(73) Assignee: Multivalent Limited, Suffolk (GB)

( * ) Notice: Subject to any disclaimer, the term of this patent is extended or adjusted under 35 U.S.C. 154(b) by 0 days.

(21) Appl. No.: 12/230,472

(22) Filed: Aug. 29, 2008

(65) Prior Publication Data

US 2009/0112012 A1    Apr. 30, 2009

(30) Foreign Application Priority Data

Oct. 27, 2007    (GB) ................................. 0721126.1

(51) Int. Cl.
*C07F 5/00*    (2006.01)
(52) U.S. Cl. ......................................................... 556/1
(58) Field of Classification Search ...................... 556/1
See application file for complete search history.

(56) References Cited

U.S. PATENT DOCUMENTS 6,426,425 B2    7/2002    Kadokura et al. ............... 556/1

FOREIGN PATENT DOCUMENTS

| JP | 08217709 | 8/1996 |
|---|---|---|
| WO | WO 91/13848 | 9/1991 |

OTHER PUBLICATIONS

Valet et al., Chemistry of Materials, vol. 13, No. 6, pp. 2135-2143 (2001).*
Carmalt et al, Coordination Chemistry Reviews, vol. 250, pp. 682-709 (2006).*

* cited by examiner

*Primary Examiner*—Porfirio Nazario Gonzalez
(74) *Attorney, Agent, or Firm*—Morgan Lewis & Bockius LLP

(57) ABSTRACT

A method of synthesising gallium or indium alkoxide from the corresponding gallium or indium halide, the method comprising the step of reacting the gallium or indium metal halide with the alkoxide of an alkali earth metal, to produce the desired metal alkoxide essentially free of chlorine contamination. The method provides a composition comprising a solution of gallium or indium alkoxide of high purity, the composition having a chloride content of less than 30 ppm, a barium or strontium content of less than 30 ppm, and a sodium or potassium content of less than 30 ppm, without requiring any additional steps.

18 Claims, No Drawings

SYNTHESIS OF GALLIUM AND INDIUM ALKOXIDES

FIELD OF THE INVENTION

The present invention relates to the production of gallium and indium alkoxides.

BACKGROUND OF THE INVENTION

Gallium and indium alkoxides are useful as precursors to their respective oxides, in isolation or combined with each other or in combination with tin and/or zinc alkoxides to form amorphous oxide semiconductors employed in thin film photovoltaic devices. The chief advantage of alkoxides over other chemical forms of the eponymous elements is low processing temperature by the sol-gel technique especially in its non-hydrolytic application (elimination of ester and/or ether condensation products). Display components fabricated by less convenient means have already been demonstrated (Nomura et al, 2006, Jpn J Appl Phys 45(5B) 4303-8).

Methods of synthesis of gallium and indium alkoxides have been reviewed by Carmalt & King (2006 Coordination Chemistry Reviews 250, 682-709).

Probably the best-known synthetic method is the reaction of the metal tri-halide with 3 equivalents of sodium alkoxide, NaOR (where R is the desired alkyl chain). This method was first taught for gallium alkoxide by Mehrotra & Mehrotra (1964 Current Sci. (India) 33, 241) and by Funk & Paul (1964 Anorg Allg. Chem. 330, 70), and subsequently for indium alkoxide by Chatterjee et al, (1976 J. Ind. Chem. Soc. 53, 867). Other methods are known, but they employ expensive reagents and lack scope for economy of scale upon commercial scale-up.

It was recently revealed (U.S. Pat. No. 6,426,425) that gallium and indium alkoxides prepared in this way are contaminated with residual chloride and such ionic impurities are terminally detrimental to the operation of subsequently fabricated electronic devices. U.S. Pat. No. 6,426,425 discloses a process for purifying gallium alkoxide (i.e. removing the chloride contaminant) by adding potassium alkoxide followed by distillation or sublimation. The resulting product has a significantly reduced level of chloride contamination, for example 200 ppm.

The present invention aims, in one object, to provide a method of synthesising an alkoxide of gallium or indium, from the corresponding halide, in such a way as to substantially avoid the presence of any contaminating halide, and thereby avoid the need for further expensive processing stages.

It is a further object to provide a method of synthesising a metal alkoxide from the corresponding halide, in such a way as to substantially avoid the product being contaminated with sodium or potassium. The synthetic method of the invention provides a particularly pure product without the need for any further reactions.

SUMMARY OF THE INVENTION

In general terms, in a first aspect, the invention provides a method of synthesising a metal alkoxide from the corresponding metal halide, the method comprising the step of reacting the metal halide with the alkoxide of an alkali earth metal, to produce the desired metal alkoxide essentially free of chlorine contamination.

For present purposes, "essentially free of chlorine contamination" means having a chloride content of less than 75 ppm, preferably less than 50 ppm, and most preferably less than 30 ppm.

The alkali earth metal alkoxide starting material preferably comprises a barium alkoxide, but may also comprise a strontium alkoxide, or a mixture of barium and strontium alkoxides.

The alkoxy group of the alkoxide may be straight-chain or branched. The alkoxy group may comprise substitutions, but is preferably unsubstituted. The carbon chain length of the alkoxy group is typically 2-6, preferably 2, 3 or 4.

As noted above, synthesis of e.g. gallium alkoxide using gallium trichloride as a starting material should, in theory, require three molar equivalents of sodium alkoxide to produce a complete product, according to the equation (1):

$$GaCl_3 + 3NaOR \rightarrow Ga(OR)_3 + 3NaCl \tag{1}$$

In practice, due to the coordination requirements of the central metal ion, the product derived from three equivalents of sodium alkoxide is shown by equation (2):

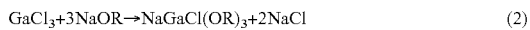
$$GaCl_3 + 3NaOR \rightarrow NaGaCl(OR)_3 + 2NaCl \tag{2}$$

It is possible to eliminate chlorine contamination of the desired gallium alkoxide by using a further equivalent sodium alkoxide, according to equation (3):

$$GaCl_3 + 4NaOR \rightarrow NaGa(OR)_4 + 3NaCl \tag{3}$$

However, it is immediately apparent that this results in a product contaminated with sodium (or potassium, if potassium alkoxide is used), which is difficult to eliminate from the compound.

In contrast, the method of the present invention results in the formation of an intermediate incorporating barium (or strontium) (equation 4), which can then be readily dissociated from the intermediate by exchanging the solvent (equation 5), leaving the desired product in substantially pure form:

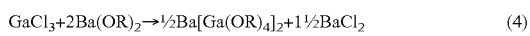
$$GaCl_3 + 2Ba(OR)_2 \rightarrow \tfrac{1}{2}Ba[Ga(OR)_4]_2 + 1\tfrac{1}{2}BaCl_2 \tag{4}$$

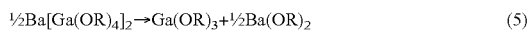
$$\tfrac{1}{2}Ba[Ga(OR)_4]_2 \rightarrow Ga(OR)_3 + \tfrac{1}{2}Ba(OR)_2 \tag{5}$$

The amount of barium (or strontium, if strontium alkoxide is employed) contaminating the gallium or indium alkoxide product which can be synthesised using the method of the present invention is typically less than 150 ppm and preferably less than 30 ppm. Sodium or potassium contamination of the product, as judged by flame photometry of a nitric acid extract, is typically less than 50 ppm, and preferably less than 5 ppm as neither of these reagents is employed in the synthetic method.

Accordingly, it is desirable (but not essential) during performance of the method of the invention, to determine the progress of the reaction (and particularly the end-point thereof) by measuring or assaying. This may conveniently be done by removing one or more aliquots as the presumed end-point is approached. Preferably the aliquot(s) may be assayed for the presence of organic solubilised chloride (e.g. by silver nitrate testing of a nitric acid-treated aliquot to determine chloride content).

In more detail, the method of the invention typically involves dissolving the metal chloride in a suitable organic solvent and adding to the dissolved metal chloride a solution of barium or strontium alkoxide. The barium or strontium alkoxide is added until testing of aliquots of the reaction mixture indicates no residual organic-soluble chloride is detected. The precipitated barium chloride can be removed by any convenient means (e.g. centrifugation or filtration). The resulting clear liquid is stripped to minimum volume, dissolved in a saturated hydrocarbon such as n-heptane, refluxed for about 2 hours then allowed to cool and settle. The dissociated barium content (precipitated as barium alkoxide) may then be removed by conventional means (e.g. centrifugation or filtration), and the product recovered by removal of solvent under vacuum.

In a second aspect, the invention provides a composition comprising a solution of gallium or indium alkoxide of high purity, the composition being prepared by the method of the first aspect, and having a chloride content of less than 30 ppm, a barium or strontium content of less than 30 ppm, and a sodium or potassium content of less than 5 ppm.

The invention will now be further described by way of illustrative examples.

COMPARATIVE EXAMPLE 1

Synthesis of Gallium Isopropoxide from 3 Mole Equivalents of Sodium Isopropoxide 220 g of gallium chloride were dissolved in 1800 ml of n-hexane and added over a period of 2 hours to a warm solution of sodium isopropoxide freshly made by dissolving 86 g of sodium in 5.5 liters of dry isopropanol. During the course of the addition the hexane fraction boiling below 80° C. was removed using a reflux splitter and the volume made up using 1.5 liter fresh, dry isopropanol. After all the hexane was removed the mixture was refluxed for 2 hours then allowed to cool and settle. The liquor was centrifuged and the clear supernatant stripped to a paste weighing 215 g, which was found to contain 2.5% chloride by silver nitrate titration of its nitric acid, extract and 1.5% sodium by flame photometry of the same solution. We conclude there is heavy contamination by a double chlorinated alkoxide that can be represented as $NaGa(OC_3H_7)_3Cl$.

COMPARATIVE EXAMPLE 2

Synthesis of Gallium Isopropoxide from 3 Mole Equivalents of Potassium Isopropoxide 133 g of potassium were dissolved in 3 liters of dry isopropanol and added over 2 hours to a refluxing solution of 200 g gallium chloride dissolved in 1.5 liters of n-hexane. During the course of the addition the hexane fraction boiling below 80° C. was removed using a reflux splitter and the volume made up using 1.5 liter fresh dry isopropanol. After all the hexane was removed the mixture was refluxed for 2 hours then allowed to cool and settle. The liquor was centrifuged and the clear supernatant stripped to a paste weighing 195 g, which was found to contain 2.5% chloride by silver nitrate titration of its nitric acid extract and 2.5% potassium by flame photometry of the same solution. We conclude there is heavy contamination by a double chlorinated alkoxide that can be represented as $KGa(OC_3H_7)_3Cl$.

COMPARATIVE EXAMPLE 3

Synthesis of Gallium Isopropoxide from 4 Mole Equivalents of Sodium Isopropoxide 220 g of gallium chloride were dissolved in 1800 ml of n-hexane and added over a period of 2 hours to a warm solution of sodium isopropoxide freshly made by dissolving 115 g of sodium in 5.5 liters of dry isopropanol. During the course of the addition the hexane fraction boiling below 80° was removed using a reflux splitter and the volume made up using 1.5 liter fresh dry isopropanol. After all the hexane was removed the mixture was refluxed for 2 hours then allowed to cool and settle. The liquor was centrifuged and the clear supernatant stripped to a paste weighing 215 g, which was found to contain no detectable chloride by silver nitrate spot test of its nitric acid extract, but 6.5% sodium by flame photometry of the same solution. We conclude the majority of the product is the double alkoxide $NaGa(OC_3H_7)_4$. It is insoluble in heptane and the sodium component could not be segregated by dissociation.

COMPARATIVE EXAMPLE 4

Synthesis of Gallium Isopropoxide from 4 Mole Equivalents of Potassium Isopropoxide 177 g of potassium were dissolved in 3 liters of dry isopropanol and added over 2 hours to a refluxing solution of 200 g gallium chloride dissolved in 1.5 liters of n-hexane. During the course of the addition the hexane fraction boiling below 80° C. was removed using a reflux splitter and the volume made up using 1.5 liter fresh dry isopropanol. After all the hexane was removed the mixture was refluxed for 2 hours then allowed to cool and settle. The liquor was centrifuged and the clear supernatant stripped to a paste weighing 205 g, which was found to contain no chloride by silver nitrate spot test of its nitric acid extract but 8.1% potassium by flame photometry of the same solution. We conclude the majority of the product is the double alkoxide $KGa(OC_3H_7)_4$. It was insoluble in heptane and the potassium component could not be separated by dissociation.

EXAMPLE 5 (IN ACCORDANCE WITH THE INVENTION)

Synthesis of Gallium Isopropoxide Using 1.75 Mole Equivalents of Barium 200 g of anhydrous gallium chloride were dissolved in 2 liters of dry isopropanol by stirring at room temperature for 4 hours. 234 g of barium were dissolved in 2 liters of dry isopropanol and the solution clarified before being added slowly to the refluxing gallium chloride solution. As the reaction proceeded the organic-soluble chloride was monitored by withdrawing small samples, centrifuging the precipitated barium chloride and dissolving the clear supernatant in 2N nitric acid and spot testing with 0.1N silver nitrate solution. The barium solution continued to be added until the spot testing indicated no organic soluble chloride. This was found to coincide with the addition of 3.5 mole equivalents of isopropoxide (or 1.75 mole equivalents of barium). The mixture was refluxed for 2 hours, allowed to cool and centrifuged free of precipitated barium chloride. The clear liquor was stripped to an oil which in contrast to the alkali metal double alkoxides is soluble in saturated hydrocarbons. The oil was dissolved in dry heptane and refluxed for 2 hours then left to cool and settle. The mixture was centrifuged and the clear supernatant stripped to crystallisation. Weight of product 210 g, chloride was not detected by silver nitrate spot test and the barium content was 95 ppm by flame photometry.

COMPARATIVE EXAMPLE 6

Synthesis of Indium Isopropoxide Using Three Mole Equivalents of Sodium 443 g of anhydrous indium chloride were dissolved in a mixture of 2 liters of dry isopropanol and 2 liters of dry dimethoxyethane by stirring at room temperature for 4 hours. This solution was added over 1 hour to a warm solution of sodium isopropoxide freshly made by dissolving 138 g of sodium in 5 liters of dry isopropanol. The mixture was refluxed for 7 hours, allowed to cool and centrifuged free of precipitated barium chloride. The clear liquor was stripped to a solid and re-dissolved in dry toluene. Meanwhile the residues are extracted in 3 liters of dry toluene, re-spun and the clear liquors combined with the original portion, concentrated to 500 ml and set aside to crystallise. A solid product weighing 355 g was obtained having a chloride content of 2.4% by silver nitrate titration of its nitric acid solution, and a sodium content of 1.6% by flame photometry of its nitric acid solution indicating heavy contamination with $NaIn(OC_3H_7)_3Cl$.

COMPARATIVE EXAMPLE 7

Synthesis of Indium Isopropoxide Using Four Mole Equivalents of Sodium 443 g of anhydrous indium chloride were dissolved in a mixture of 2 liters of dry isopropanol and 2 liters of dry dimethoxyethane by stirring at room temperature for 4 hours. This solution was added over 1 hour to a warm solution of sodium isopropoxide freshly made by dissolving 184 g of sodium in 5 liters of dry isopropanol. The mixture was refluxed for 7 hours, allowed to cool and centrifuged free of precipitated sodium chloride. The clear liquor was stripped to a solid and re-dissolved in dry toluene. Meanwhile the residues were extracted in 3 liters of dry toluene, re-spun and the clear liquors combined with the original portion, concentrated to 500 ml and set aside to crystallise. A solid product weighing 370 g was obtained having a negligible chloride content by addition of silver nitrate solution to its nitric acid solution, but a sodium content of 3.5% by flame photometry of nitric acid solution, indicating an approximately 50% contamination by the mixed metal alkoxide $NaIn(OC_3H_7)_4$. It was insoluble in heptane and the sodium component could not be separated by dissociation.

EXAMPLE 8 (IN ACCORDANCE WITH THE INVENTION)

Synthesis of Indium Isopropoxide Using 1.75 Mole Equivalents of Barium 200 g of anhydrous indium chloride were dissolved in 2 liters of dry isopropanol by stirring at room temperature for 4 hours. 186 g of barium were dissolved in 2 liters of dry isopropanol and the solution clarified before being added slowly to the refluxing indium chloride solution. As the reaction proceeded the organic-soluble chloride was monitored by withdrawing small samples, centrifuging the precipitated barium chloride and dissolving the clear supernatant in 2N nitric acid and spot testing with 0.1N silver nitrate solution. The barium solution continued to be added until the spot testing indicated no organic soluble chloride. This was found to coincide with the addition of 3.5 mole equivalents of isopropoxide (or 1.75 mole equivalents of barium). The mixture was refluxed for 2 hours, allowed to cool and centrifuged free of precipitated barium chloride. The clear liquor was stripped to a solid, re-dissolved in dry heptane and refluxed for another two hours then left to cool and settle. This solution was centrifuged and the clear supernatant stripped to crystallisation. Weight of product 205 g, chloride not detected by silver nitrate spot test, barium content 125 ppm by flame photometry.

The invention claimed is:

1. A method of synthesising gallium or indium alkoxide from the corresponding gallium or indium halide, the method comprising the step of reacting the gallium or indium metal halide with the alkoxide of an alkali earth metal, to produce the desired metal alkoxide essentially free of chlorine contamination.

2. A method according to claim 1, wherein the metal halide comprises a tri-halide.

3. A method according to claim 2, wherein the metal halide comprises a tri-chloride.

4. A method according to claim 1, wherein the alkali earth metal comprises barium and/or strontium.

5. A method according to claim 1, wherein the halide groups of the metal halide are substituted by the alkoxy groups of the alkali earth metal alkoxide.

6. A method according to claim 5, wherein each alkoxy group of the alkoxide comprises 2-6 carbon atoms.

7. A method according to claim 6, wherein each alkoxy group comprises 2-4 carbon atoms.

8. A method according to claim 1, wherein the metal alkoxide is homoleptic.

9. A method according to claim 1, further comprising monitoring or measuring the progress of the reaction of the metal halide with the alkali earth metal alkoxide, and/or determining the end-point of the reaction.

10. A method according to claim 9, wherein the monitoring, measuring or determining the end-point comprises testing an aliquot of a reaction mixture for the presence of organic solubilised chloride.

11. A method according to claim 10, wherein the aliquot is treated with nitric acid and tested with silver nitrate solution for the presence of chloride.

12. A method according to claim 9, wherein addition of barium or strontium alkoxide to a reaction mixture is halted substantially simultaneously with reaching the end-point of the reaction.

13. A method according to claim 1, wherein the metal halide is present in solution, and a solution of the alkali earth metal alkoxide is contacted with the solution of metal halide.

14. A method according to claim 1, wherein the reaction forms an alkali earth metal halide which is precipitated.

15. A method according to claim 14, wherein the precipitated alkali earth metal halide is removed and the remaining liquid is dissolved in a saturated hydrocarbon solvent and refluxed, to precipitate an alkali earth metal alkoxide.

16. A method according to claim 15, wherein the saturated hydrocarbon solvent comprises heptane.

17. A method according to claim 14, wherein precipitated material is removed from a reaction mixture by centrifugation or filtration.

18. A method according to claim 1, performance of which produces a metal alkoxide having a chloride content of less than 30 ppm, a barium or strontium content of less than 30 ppm, and a sodium or potassium content of less than 5 ppm, without requiring any additional purification steps.

* * * * *